United States Patent
Greiveldinger-Poenaru et al.

(10) Patent No.: US 7,524,854 B2
(45) Date of Patent: Apr. 28, 2009

(54) BENZOFURAN DERIVATIVES AND THEIR USE IN THE TREATMENT OF MICROBIAL INFECTIONS

(75) Inventors: Sorana Greiveldinger-Poenaru, Rheinfelden (CH); Khalid Islam, Reinach (CH); Dieter Gillessen, Pratteln (CH); Kaspar Burri, Binningen (CH)

(73) Assignee: Arpida AG (CH)

( * ) Notice: Subject to any disclaimer, the term of this patent is extended or adjusted under 35 U.S.C. 154(b) by 442 days.

(21) Appl. No.: 10/563,938

(22) PCT Filed: Jul. 8, 2004

(86) PCT No.: PCT/EP2004/007482

§ 371 (c)(1), (2), (4) Date: Jan. 10, 2006

(87) PCT Pub. No.: WO2005/005418

PCT Pub. Date: Jan. 20, 2005

(65) Prior Publication Data

US 2006/0154943 A1    Jul. 13, 2006

(30) Foreign Application Priority Data

Jul. 11, 2003    (WO) ..................... PCT/EP03/07537

(51) Int. Cl.
*C07D 407/14* (2006.01)
*A61K 31/506* (2006.01)

(52) U.S. Cl. ...................... 514/275; 544/324

(58) Field of Classification Search ................ 544/324; 514/275

See application file for complete search history.

(56) References Cited

FOREIGN PATENT DOCUMENTS

| EP | A-0 051 879 | 5/1982 |
| EP | A-0 096 214 | 12/1983 |
| WO | WO-02/10156 | 2/2002 |
| WO | WO-02/10157 | 2/2002 |

OTHER PUBLICATIONS

Snyder et al., PubMed Abstract (J Med Liban. 48(4):208-14) Jul.-Aug. 2000.*

* cited by examiner

*Primary Examiner*—Deepak Rao
(74) *Attorney, Agent, or Firm*—Dickstein, Shapiro, LLP.

(57) ABSTRACT

The invention relates to new benzofuran derivatives and their use as active ingredients in the preparation of pharmaceutical compositions. The invention also concerns related aspects including processes for the preparation of the compounds, pharmaceutical compositions containing one or more of those compounds and especially their use as anti-infectives.

15 Claims, No Drawings

BENZOFURAN DERIVATIVES AND THEIR USE IN THE TREATMENT OF MICROBIAL INFECTIONS

The present invention relates to novel 2,4-diamino-5-(substituted)pyrimidines, to pharmaceutical compositions containing them, to processes for preparing them and their compositions, to intermediates for making them and to their use in the treatment of microbial infections.

Certain 2,4-diamino-5-benzylpyrimidines have been demonstrated to be potent inhibitors of dihydrofolate reductase (DHFR), which catalyses the reduction of dihydrofolic acid to tetrahydrofolic acid (THFA). This property has been shown to result frequently in useful pharmaceutical properties particularly in the treatment of bacterial infections. Thus, U.K. Patent Specification No. 875,562 discloses inter alia 2,4-diamino-5-benzylpyrimidines wherein the benzyl moiety is substituted by three $C_{1-4}$ alkoxy groups.

Trimethoprim, 2,4-diamino-5-(3,4,5-trimethoxybenzyl) pyrimidine, is specifically disclosed in U.K. Patent No. 875,562 and is the most active antibacterial agent amongst the 2,4-diamino-5-benzylpyrimidines known to date. Due to their mode of action, these benzylpyrimidines potentiate the antibacterial activity of the sulphonamides, and Trimethoprim has been used extensively over the last decade in human therapy in combination with various sulphonamides, and in particular with sulphamethoxazole, for the treatment of bacterial infections.

European Patent Applications Nos. 81109631.2 and 83104240.3 disclose inter alia also such type of compounds and their use.

In WO 02/10157 similar compounds are described. However, the compounds disclosed hereinafter exhibit a much more potent activity against DHFR including mutated enzyme, a superior bioavailability, and a superior antibacterial activity.

It has now been found that a group of novel benzofuran derivatives are more potent than, e. g., Trimethoprim, and are active against Gram positive pathogens (*Staphylococcus aureus, Staphylococcus epidermidis, Enterococcus faecalis* or *Streptococcus pneumoniae*) and Gram negative pathogens (*Haemophilus influenzae, Escherichia coli, Klebsiella pneumoniae, Moraxella Cattharalis* or *Proteus vulgaris*). Furthermore, and as mentioned above, the compounds of formula I show a much more potent activity against DHFR including mutated enzyme, a superior bioavailability, and a superior antibacterial activity.

Therefore, the present invention relates to novel compounds of the general formula I

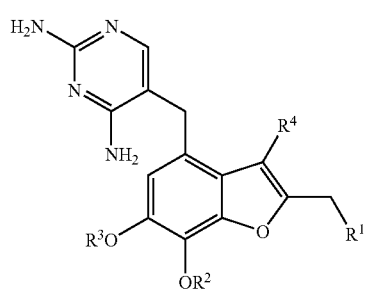

Formula I wherein
R1 represents the groups

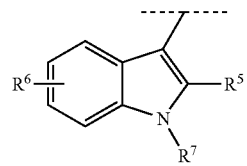

whereby in these groups $R^5$ is hydrogen, lower alkyl with 1 to 4 carbon atoms, or the group

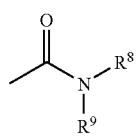

$R^8$ represents lower alkyloxy, lower alkylamino, or lower alkyl with 1 to 4 carbon atoms;
$R^9$ represents lower alkyl with 1 to 4 carbon atoms;
$R^8$ and $R^9$ together form a 5- or 6-membered heterocyclic ring containing one to two hetero atoms which can be the same or different and are oxygen or nitrogen.
$R^6$ represent hydrogen, halogen, nitro, or lower alkyloxy;
$R^7$ represents hydrogen;
$R^2$ and $R^3$ independently represent hydrogen; lower alkyl with 1 to 3 carbon atoms; or together a lower alkylene group with 1 to 3 carbon atoms bridging the oxygen atoms and forming a five, six or seven membered ring;
$R^4$ represents hydrogen;
and pharmaceutically acceptable salts thereof.

The present invention relates to novel compounds of the general formula I'

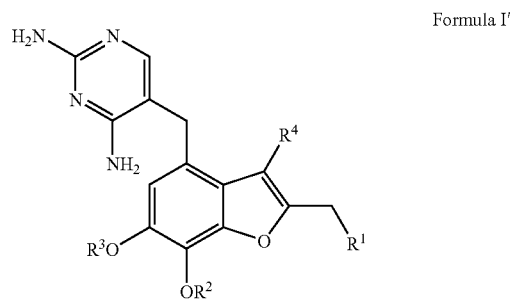

Formula I' wherein
R1 represents the groups

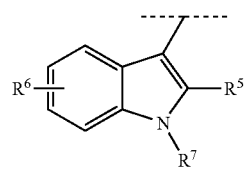

whereby in these groups $R^5$ is hydrogen, lower alkyl with 1 to 4 carbon atoms, or the group $R^8$ represents lower alkyloxy, or lower alkyl with 1 to 4 carbon atoms;

$R^9$ represents lower alkyl with 1 to 4 carbon atoms;

$R^8$ and $R^9$ together form a 5- or 6-membered heterocyclic ring containing one to two hetero atoms which can be the same or different and are oxygen or nitrogen.

$R^6$ represent hydrogen, halogen, nitro, or lower alkyloxy;

$R^7$ represents hydrogen;

$R^2$ and $R^3$ independently represent hydrogen; lower alkyl with 1 to 3 carbon atoms; or together a lower alkylene group with 1 to 3 carbon atoms bridging the oxygen atoms and forming a five, six or seven membered ring;

$R^4$ represents hydrogen;

and pharmaceutically acceptable salts thereof.

In the definitions of the general formula I—if not otherwise stated—the expression lower alkyl means straight and branched alkyl chain groups with one to four carbon atoms, preferably 1 to 2 carbon atoms. Examples of lower alkyl and groups are methyl, ethyl, n-propyl, isopropyl, n-butyl, isobutyl, sec.-butyl, tert.-butyl. These lower alkyl groups may be substituted with halogen atoms or hydroxy, thiol or lower alkoxy groups. Examples are trifluoromethyl, chloromethyl, fluoromethyl, hydroxymethyl, thiomethyl, methoxy, ethoxy, propoxy, butoxy, iso-butoxy, sec.-butoxy and tert.-butoxy The expressions lower alkylamino and lower alkoxy are compounds consisting of —NH-lower alkyl and —O-lower alkyl wherein the alkyl group is define as above. The expression heterocyclic ring represents saturated and unsaturated, but not aromatic, five- or six-membered rings containing one to two hetero atoms which may be the same or different and are nitrogen or oxygen atoms. Examples are piperidinyl, morpholinyl, piperazinyl, pyrrolidinyl, dihydroimidazolyl, dihydropyrazoyl, pyrazolidinyl or dihydroxazolinyl.

The expression halogen means fluorine, chlorine, bromine, and iodine but fluorine, chlorine and bromine are preferred.

One preferred group of compounds of the present invention are compounds of the general formula II Formula II wherein
$R^2$ and $R^3$ represent methyl;
$R^4$ represents hydrogen;
$R^5$ and $R^6$ are as defined in formula I and;
$R^7$ represents hydrogen.

A further preferred group of compounds of the present invention are compounds of the general formula III Formula III wherein
$R^2$ and $R^3$ represent methyl;
$R^4$ represents hydrogen;
$R^5$ and $R^6$ are as defined in formula I and;
$R^7$ represents hydrogen.

A further preferred group of compounds of the present invention are compounds of the general formula IV Formula IV wherein
$R^2$ and $R^3$ represent methyl;
$R^4$ represents hydrogen;
$R^5$ and $R^6$ are as defined in formula I and;
$R^7$ represents hydrogen.

Preferred compounds are compounds of formula I, I', II, III and IV wherein $R^5$ is hydrogen, methyl, carboxylic acid dimethylamide, carboxylic acid methoxymethylamide, pyrrolidin-1-yl-methanone, morpholin-4-yl-methanone, or carboxylic acid N,N'-dimethyl-hydrazide;

$R^6$ represent hydrogen, fluoro, chloro, bromo, methoxy, or nitro;

Especially preferred compounds are compounds selected from the group consisting of:

5-[6,7-Dimethoxy-2-(7-methoxy-1H-indol-3-ylmethyl)-benzofuran-4-ylmethyl]-pyrimidine-2,4-diamine;

5-[6,7-Dimethoxy-2-(5-methoxy-1H-indol-3-ylmethyl)-benzofuran-4-ylmethyl]-pyrimidine-2,4-diamine;

5-[2-(1H-indol-3-ylmethyl)-6,7-dimethoxy-benzofuran-4-ylmethyl]-pyrimidine-2,4-diamine;

5-[6,7-Dimethoxy-2-(2-methyl-1H-indol-3-ylmethyl)-benzofuran-4-ylmethyl]-pyrimidine-2,4-diamine;

5-[2-(6-Fluoro-1H-indol-3-ylmethyl)-6,7-dimethoxy-benzofuran-4-ylmethyl]-pyrimidine-2,4-diamine;

{3-[4-(2,4-Diamino-pyrimidin-5-ylmethyl)-6,7-dimethoxy-benzofuran-2-ylmethyl]-1H-indol-2-yl}-morpholin-4-yl-methanone;

3-[4-(2,4-Diamino-pyrimidin-5-ylmethyl)-6,7-dimethoxy-benzofuran-2-ylmethyl]-1H-indole-2-carboxylic acid dimethylamide;

5-[6,7-Dimethoxy-2-(5-nitro-1H-indol-3-ylmethyl)-benzofuran-4-ylmethyl]-pyrimidine-2,4-diamine;

{3-[4-(2,4-Diamino-pyrimidin-5-ylmethyl)-6,7-dimethoxy-benzofuran-2-ylmethyl]-1H-indol-2-yl}-pyrrolidin-1-yl-methanone;

3-[4-(2,4-Diamino-pyrimidin-5-ylmethyl)-6,7-dimethoxy-benzofuran-2-ylmethyl]-5-methoxy-1H-indole-2-carboxylic acid dimethylamide;

3-[4-(2,4-Diamino-pyrimidin-5-ylmethyl)-6,7-dimethoxy-benzofuran-2-ylmethyl]-1H-indole-2-carboxylic acid methoxy-methyl-amide;

5-Chloro-3-[4-(2,4-diamino-pyrimidin-5-ylmethyl)-6,7-dimethoxy-benzofuran-2-ylmethyl]-1H-indole-2-carboxylic acid dimethylamide;

3-[4-(2,4-Diamino-pyrimidin-5-ylmethyl)-6,7-dimethoxy-benzofuran-2-ylmethyl]-5-fluoro-1H-indole-2-carboxylic acid dimethylamide;

5-Chloro-3-[4-(2,4-diamino-pyrimidin-5-ylmethyl)-6,7-dimethoxy-benzofuran-2-ylmethyl]-1H-indole-2-carboxylic acid methoxy-methyl-amide;

3-[4-(2,4-Diamino-pyrimidin-5-ylmethyl)-6,7-dimethoxy-benzofuran-2-ylmethyl]-1H-indole-2-carboxylic acid N,N'-dimethyl-hydrazide;

3-[4-(2,4-Diamino-pyrimidin-5-ylmethyl)-6,7-dimethoxy-benzofuran-2-ylmethyl]-5-fluoro-1H-indole-2-carboxylic acid methoxy-methyl-amide;

The invention also relates to a process for the manufacture of compounds of the general formula I

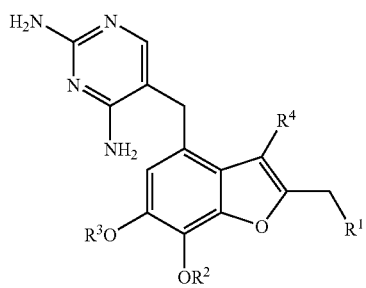

Formula I

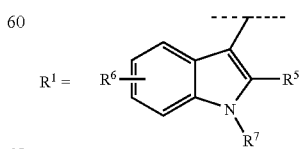

wherein
$R^1$ represents the group

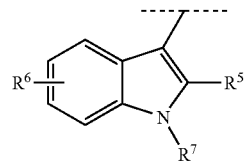

wherein
$R^7$ represents hydrogen
$R^2$, $R^3$, $R^4$, $R^5$ and $R^6$ have the meaning given in formula I above which process comprises reacting—as depicted in Scheme 1—a compound of the general formula V (see PCT Publication WO 02/10157), with the MgBr salt VII of the corresponding indoles VI.

Scheme 1

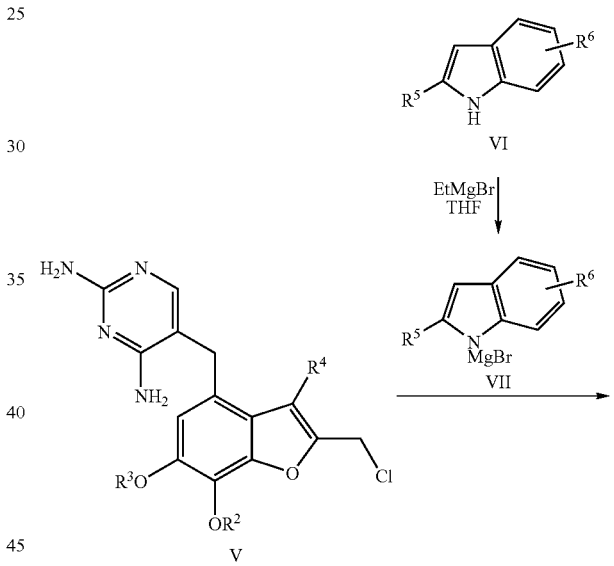

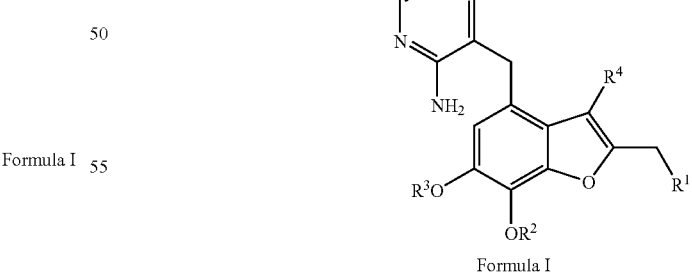

Formula I

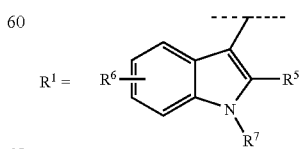

Some of the indoles of general formula VI,

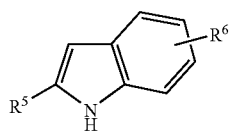

wherein $R^5$ represents the group

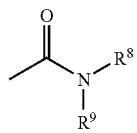

and $R^6$, $R^8$ and $R^9$ have the meaning given in formula I above, are synthesised by reacting the indoles VIII with the corresponding amine IX using EDC and HOBT as activating reagents as described in Scheme 2. The indoles VI so obtained are coupled to the compounds V using the same procedure as described above in Scheme 1 to give the compound of general formula I.

Scheme 2

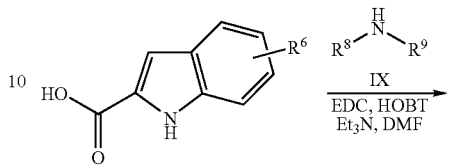

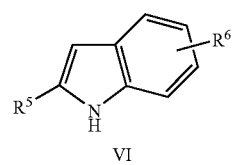

Access to an alternative array of substituents can be achieved by proceeding according to Scheme 3

Scheme 3

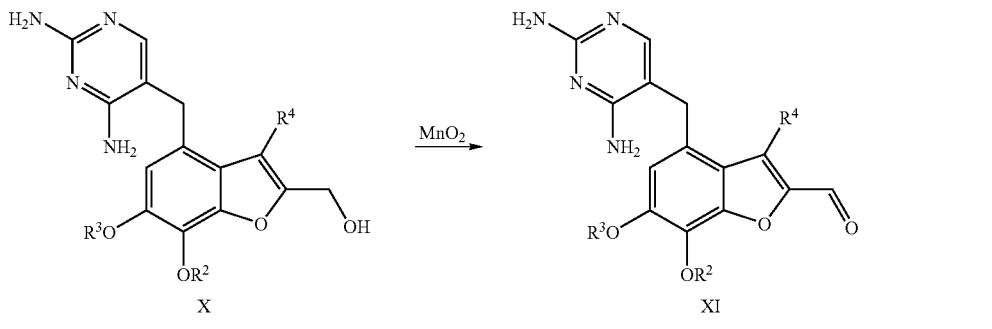

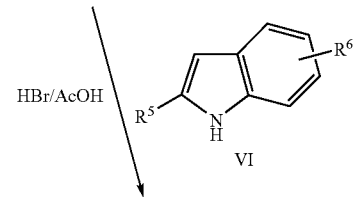

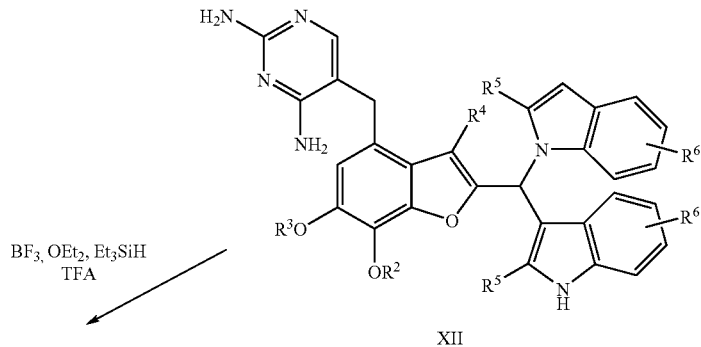

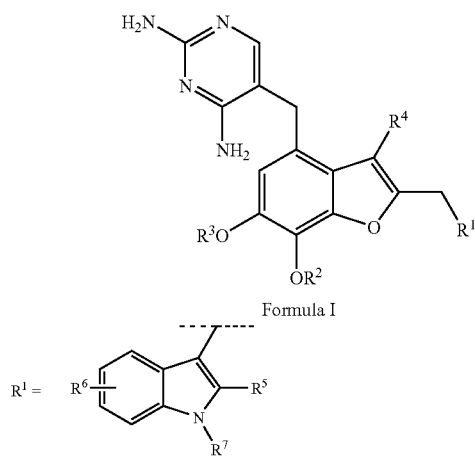

Formula I $R^1 =$ 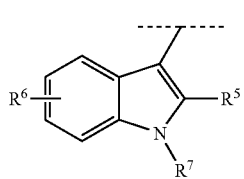

The intermediates of the general formula XI and XII are novel compounds which serve as intermediates in the synthesis of active compounds of general formula I. The alcohol X (see PCT Publication WO 02/10157) was oxidised to the aldehyde XI with MnO₂ and further coupling under acidic conditions (HBr in acetic acid) with the indoles VI resulted in the dimeric compounds of general formula XII. Reduction of compounds XII using trifluoroborane etherate and triethylsilane gave the compound of general formula I as described in Scheme 3

The invention also relates to a process for the manufacture of compounds of the general formula I

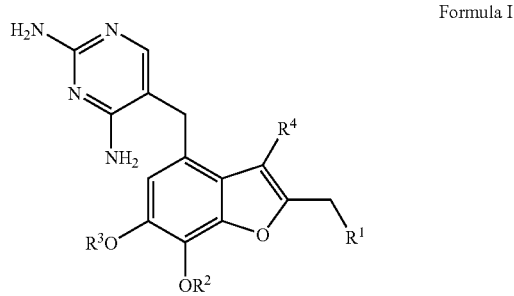

Formula I wherein $R^1$ represents the group

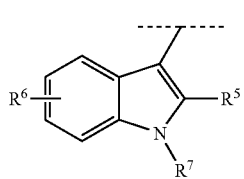

and $R^2$, $R^3$, $R^4$, $R^5$ and $R^6$ have the meaning given in formula I above, which process comprises reacting—as depicted in Scheme 4—a compound of the general formula V (see PCT Publication WO 02/10157), with the corresponding indole moiety VI under basic conditions.

Scheme 4

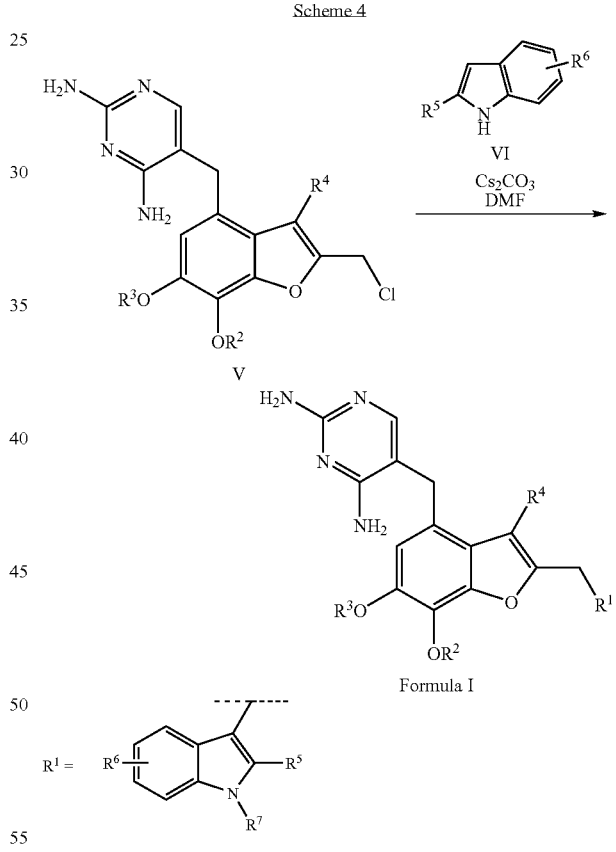

EXPERIMENTAL PARTS

Abbreviations
ACN: Acetonitrile
ATCC: American type culture collection
DMF: Dimethyl formamide
DMSO: dimethyl sulfoxide
EtOH: Ethanol
ESI: Electrospray ionisation FC. Flash chromatography
HPLC: High performance liquid chromatography
MeOH: methanol
MS: Mass spectrometry
NMR: Nuclear magnetic resonance
TBME: tert-Butyl methyl ether
TFA: Trifluoroacetic acid
THF: Tetrahydrofuran
TLC: Thin layer chromatography
EDC: N-Ethyl-N'(3-dimethylaminopropyl)carbodiimide hdrochoric acid salt
HOBT: 1-Hydroxybenzotrialzole
Et$_3$N: triethylamine
Eq.: equivalent The preparation of indoles VI which are not described in the following examples are known from the references: Young, J. Chem. Soc. 1958, 3493-3494; Finger et al. J. Amer. Chem. Soc. 1959, 81, 94-97; Dekhane M., Dodd, R. H., Tetrahedron, 1994, 50, 21, 6299-6306.

General Procedure A: Amide Coupling (Scheme 2)

Under nitrogen, at room temperature and in a flask adapted with a mechanical stirrer, indole-carboxylic acid VIII (1 eq.) was dissoveld in DMF. To this solution, the corresponding amine IX (1.1 to 5 eq.) EDC (1.2 eq), HOBT (1.2 eq) and were added followed by triethylamine (3 eq.).The mixture was stirred overnight at room temperature. After the reaction is completed, the mixture was poured slowly to a NaHCO$_3$ solution. After extration with dichloromethane the organic layer was washed with 1 N HCl, and brine, dried on MgSO$_4$ and evaporated under reduced pressure. The compound VI was obtained as a solid and was used without further purification.

EXAMPLE 1

5-Chloro-1H-indole-2-carboxylic acid dimethylamide (633 mg, 55%) was obtained by reacting 5-chloro-1H-Indole-2-carboxylic acid (1.0 g, 5.10 mmol) with dimethylamine hydrochloride (500 mg, 6.13 mmol), EDC (1.175 g, 6.13 mmol) and HOBT (826 mg, 6.13 mmol).

MS ESI m/z:: 223.0 [M+H]$^+$.

EXAMPLE 2

5-Fluoro-1H-indole-2-carboxylic acid dimethylamide (791 mg, 69%) was obtained by reacting 5-fluoro-1H-Indole-2-carboxylic acid (1.0 g, 5.60 mmol) with dimethylamine hydrochloride (550 mg, 6.72 mmol), EDC (1.30 g, 6.72 mmol) and HOBT (910 mg, 6.72 mmol).

MS ESI m/z:: 207.0 [M+H]$^+$.

EXAMPLE 3

1H-indole-2-carboxylic acid N,N'-dimethyl-hydrazide (937 mg, 92%) was obtained by reacting 1H-Indole-2-carboxylic acid (1.0 g, 6.20 mmol) with N,N'-dimethyl-hydrazine (980 mg, 7.40 mmol), EDC (1.43 g, 7.40 mmol) and HOBT (1.01 g, 7.40 mmol).

MS ESI m/z:: 204.0 [M+H]$^+$.

EXAMPLE 4

5-Fluoro-1H-indole-2-carboxylic acid methoxy-methyl-amide (2.85 g, 76%) was obtained by reacting 5-fluoro-1H-Indole-2-carboxylic acid (3.0 g, 16.74 mmol) with O,N-dim-ethyl-hydroxylamine (2.45 g, 25.11 mmol), EDC (3.85 g, 20.09 mmol) and HOBT (2.71 g, 20.09 mmol).

MS ESI m/z:: 223.0 [M+H]$^+$.

EXAMPLE 5

5-Chloro-1H-indole-2-carboxylic acid methoxy-methyl-amide (952 mg, 78%) was obtained by reacting 5-chloro-1H-Indole-2-carboxylic acid (1.0 g, 5.10 mmol) with O,N-dimethyl-hydroxylamine (600 mg, 6.13 mol), EDC (1.17 g, 6.13 mmol) and HOBT (826 mg, 6.13 mmol).

MS ESI m/z:: 239.0 [M+H]$^+$.

General Procedure B: Coupling of the Indols with Compound V (Scheme 4)

To a solution of VI (1.1 eq) in dimethylformamide, cesium carbonate (3.0 eq) or potassium carbonate was added portionwise at room temperature under argon. Compound V (1.0 eq) was added and the mixture was stirred for 2 hours at room temperature until completion. The reaction mixture was quenched with a solution saturated of NaHCO$_3$ and extracted with dichloromethane. The organic layer was washed with water, solution saturated of NaCl, dried over MgSO$_4$ and evaporated under reduced pressure. The compound I was obtained after purification by FC, gradient from CH$_2$Cl$_2$ to CH$_2$Cl$_2$/methanol (9/1).

EXAMPLE 6

5-[2-(1H-indol-3-ylmethyl)-6,7-dimethoxy-benzofuran-4-ylmethyl]-pyrimidine-2,4-diamine (40 mg, 23%) was obtained as a brown solid by reacting 5-(2-chloromethyl-6,7-dimethoxy-benzofuran-4-ylmethyl)-pyrimidine-2,4-di-amine (153 mg, 0.397 mmol) with cesium carbonate (388 mg, 1.19 mmol) and indole (51 mg, 0.437 mmol).

MS ESI m/z:: 430.2 [M+H]$^+$; Structure confirmed by $^1$H NMR 400 MHz in DMSO-d$_6$.

EXAMPLE 7

5-[6,7-Dimethoxy-2-(7-methoxy-1H-indol-3-ylmethyl)-benzofuran-4-ylmethyl]-pyrimidine-2,4-diamine (120 mg, 62%) was obtained as a yellow solid by reacting 5-(2-chloromethyl-6,7-dimethoxy-benzofuran-4-ylmethyl)-pyrimidine-2,4-diamine (163 mg, 0.342 mmol) with cesium carbonate (413 mg, 1.26 mmol) and 7-Methoxy-1H-indole (68 mg, 0.465 mmol).

MS ESI m/z:: 460.2 [M+H]$^+$.

EXAMPLE 8

5-[6,7-Dimethoxy-2-(5-methoxy-1H-indol-3-ylmethyl)-benzofuran-4-ylmethyl]-pyrimidine-2,4-diamine (30 mg, 18%) was obtained as a brown solid by reacting 5-(2-chloromethyl-6,7-dimethoxy-benzofuran-4-ylmethyl)-pyrimidine-2,4-diamine (140 mg, 0.363 mmol) with cesium carbonate (355 mg, 1.09 mmol) and 5-methoxy-1H-indole (59 mg, 0.400 mmol).

MS ESI m/z:: 460.2 [M+H]$^+$.

EXAMPLE 9

5-[6,7-Dimethoxy-2-(2-methyl-1H-indol-3-ylmethyl)-benzofuran-4-ylmethyl]-pyrimidine-2,4-diamine (27 mg, 16%) was obtained by reacting 5-(2-chloromethyl-6,7-dimethoxy-benzofuran-4-ylmethyl)-pyrimidine-2,4-di-amine (151 mg 0.392 mmol) with cesium carbonate (383 mg, 1.17 mmol) and 2-methyl-1H-indole (56 mg, 0.431 mmol).

MS ESI m/z:: 444.2 [M+H]$^+$.

EXAMPLE 10

5-[2-(6-Fluoro-1H-indol-3-ylmethyl)-6,7-dimethoxy-benzofuran-4-ylmethyl]-pyrimidine-2,4-diamine (31 mg, 13%) was obtained by reacting 5-(2-chloromethyl-6,7-dimethoxy-benzofuran-4-ylmethyl)-pyrimidine-2,4-diamine (202 mg, 0.524 mmol) with cesium carbonate (607 mg, 1.573 mmol) and 6-fluoro-1H-indole (78 mg, 0.577 mmol).

MS ESI m/z:: 448.2 [M+H]$^+$.

General Procedure C: Coupling of the Indols with Compound V (Scheme 1)

To a suspension of VI (6.0 eq) in tetrahydrofurane freshly distilled, a 4.2M-solution of ethyl magnesium bromide in diethyl ether (6.0 eq) was added at 0° C. under an argon flux. After stirring 1 hour at 0° C., diethyl ether was added to the resulting mixture to give the compound VII as a beige precipitate. After decantation, the excess of solvent was removed and the compound VII was suspended in dichloromethane.

To this suspension, the compound V (1.0 eq) was added portionwise at room temperature under argon and the mixture was stirred overnight. The reaction was complete after stirring 16 hours at room temperature. The resulting mixture was quenched with water and extracted with dichloromethane. The organic layer was washed with a solution saturated of NaHCO$_3$, with a solution saturated of NaCl, dried over MgSO$_4$ and evaporated. The compound I was obtained after purification by FC, gradient from CH$_2$Cl$_2$ to CH$_2$Cl$_2$/methanol (9/1).

EXAMPLE 11

{3-[4-(2,4-Diamino-pyrimidin-5-ylmethyl)-6,7-dimethoxy-benzofuran-2-ylmethyl]-1H-indol-2-yl}-morpholin-4-yl-methanone (42 mg, 15%) was obtained by reacting 5-(2-chloromethyl-6,7-dimethoxy-benzofuran-4-ylmethyl)-pyrimidine-2,4-diamine (197 mg, 0.511 mmol) with the salt of 1H-indol-2-yl)-morpholin-4-yl-methanone obtained by reacting a 4.2M-solution of ethyl magnesium bromide in diethyl ether (0.716 mL, 3.07 mmol) and (1H-indol-2-yl)-morpholin-4-yl-methanone (706 mg, 3.07 mmol).

MS ESI m/z: 543.1 [M+H]$^+$.

EXAMPLE 12

3-[4-(2,4-Diamino-pyrimidin-5-ylmethyl)-6,7-dimethoxy-benzofuran-2-ylmethyl]-1H-indole-2-carboxylic acid dimethylamide (43 mg, 17%) was obtained by reacting 5-(2-chloromethyl-6,7-dimethoxy-benzofuran-4-ylmethyl)-pyrimidine-2,4-diamine (191 mg, 0.496 mmol) with the salt of H-indole-2-carboxylic acid dimethylamide obtained by reacting a 4.2M-solution of ethyl magnesium bromide in diethyl ether (0.695 mL, 2.97 mmol) and 1H-indole-2-carboxylic acid dimethylamide (560 mg, 2.97 mmol).

MS ESI M/Z:: 501.2 [M+H]$^+$; Structure confirmed by $^1$H NMR 400 MHz in DMSO-d$_6$.

EXAMPLE 13

5-[6,7-Dimethoxy-2-(5-nitro-1H-indol-3-ylmethyl)-benzofuran-4-ylmethyl]-pyrimidine-2,4-diamine (48 mg, 26%) was obtained by reacting 5-(2-chloromethyl-6,7-dimethoxy-benzofuran-4-ylmethyl)-pyrimidine-2,4-diamine (153 mg, 0.389 mmol) with the salt of 5-nitro-1H-indole obtained by reacting a 3M-solution of ethyl magnesium bromide in diethyl ether (0.783 mL, 2.33 mmol) and 5-nitro-1H-indole (379 mg, 2.33 mmol).

MS ESI m/z: 475.2 [M+H]$^+$.

General Procedure D: Coupling of the Indols with Compound V (Scheme 1)

To a suspension of VI (6.0 eq) in tetrahydrofurane freshly distilled, a 4.2M-solution of ethyl magnesium bromide in diethyl ether (6.0 eq) was added at 0° C. under an argon flux. After 1 hour at this temperature, diethyl ether was added to the resulting mixture to give the compound VII as a beige precipitate. After decantation, the excess of solvent was removed and the compound VII was suspended in dichloroethane.

To this suspension, the compound V (1.0 eq) was added portionwise at room temperature under argon, zinc chloride (1 eq) was added and the reaction mixture was heated at 70° C. until the reaction was complete. The resulting mixture was quenched with water and extracted with dichloromethane. The organic layer was washed with a solution saturated of NaHCO$_3$, with a solution saturated of NaCl, dried over MgSO$_4$ and evaporated. The compound I was obtained after purification by FC, gradient from CH$_2$Cl$_2$ to CH$_2$Cl$_2$/methanol (9/1).

EXAMPLE 14

{3-[4-(2,4-Diamino-pyrimidin-5-ylmethyl)-6,7-dimethoxy-benzofuran-2-ylmethyl]-1H-indol-2-yl}-pyrrolidin-1-yl-methanone (34 mg, 18%) was obtained by reacting 5-(2-chloromethyl-6,7-dimethoxy-benzofuran-4-ylmethyl)-pyrimidine-2,4-diamine (136 mg, 0.355 mmol) with zinc chloride (48 mg, 0.355 mmol) and the salt of (1H-indol-2-yl)-pyrrolidin-1-yl-methanone obtained by reactiong a 3M-solution of ethyl magnesium bromide in diethyl ether (0.710 mL, 2.13 mmol) and (1H-indol-2-yl)-pyrrolidin-1-yl-methanone (457 mg, 2.13 mmol).

MS ESI m/z: 527.1 [M+H]$^+$.

EXAMPLE 15

3-[4-(2,4-Diamino-pyrimidin-5-ylmethyl)-6,7-dimethoxy-benzofuran-2-ylmethyl]-5-methoxy-1H-indole-2-carboxylic acid dimethylamide (18 mg, 11%) was obtained by reacting 5-(2-chloromethyl-6,7-dimethoxy-benzofuran-4-ylmethyl)-pyrimidine-2,4-diamine (113 mg, 0.295 mmol) with zinc chloride (40 mg, 0.295 mmol) and the salt of 5-methoxy-1H-indole-2-carboxylic acid dimethylamide obtained by reacting a 3M-solution of ethyl magnesium bromide in diethyl ether (0.590 mL, 1.7 mmol), and 5-methoxy-1H-indole-2-carboxylic acid dimethylamide (386 mg, 1.77 mmol).

MS ESI m/z: 531.1 [M+H]$^+$.

EXAMPLE 16

3-[4-(2,4-Diamino-pyrimidin-5-ylmethyl)-6,7-dimethoxy-benzofuran-2-ylmethyl]-1H-indole-2-carboxylic acid methoxy-methyl-amide (18 mg, 6%) was obtained by reacting 5-(2-chloromethyl-6,7-dimethoxy-benzofuran-4-ylmethyl)-pyrimidine-2,4-diamine (198 mg, 0.513 mmol) with zinc chloride (70 mg, 0.513 mmol) and the salt of 1H-indole-2-carboxylic acid methoxy-methyl-amide obtained by reacting a 3M-solution of ethyl magnesium bromide in diethyl ether (1.03 mL, 3.08 mmol), and 1H-indole-2-carboxylic acid methoxy-methyl-amide (629 mg, 3.08 mmol).

MS ESI M/Z:: 517.2 [M+H]+; Structure confirmed by 1H NMR 400 MHz in DMSO-d6.

EXAMPLE 17

5-Chloro-3-[4-(2,4-diamino-pyrimidin-5-ylmethyl)-6,7-dimethoxy-benzofuran-2-ylmethyl]-1H-indole-2-carboxylic acid dimethylamide (9 mg, 3%) was obtained by reacting 5-(2-chloromethyl-6,7-dimethoxy-benzofuran-4-ylmethyl)-pyrimidine-2,4-diamine (183 mg, 0.476 mmol) with zinc chloride (65 mg, 0.476 mmol) and the salt of 5-chloro-1H-indole-2-carboxylic acid dimethylamide obtained by reacting a 3M-solution of ethyl magnesium bromide in diethyl ether (0.95 mL, 2.86 mmol), and 5-chloro-1H-indole-2-carboxylic acid dimethylamide (636 mg, 2.86 mmol).

MS ESI m/z: 535.2 [M+H]+; Structure confirmed by 1H NMR 400 MHz in DMSO-d6.

EXAMPLE 18

3-[4-(2,4-Diamino-pyrimidin-5-ylmethyl)-6,7-dimethoxy-benzofuran-2-ylmethyl]-5-fluoro-1H-indole-2-carboxylic acid dimethylamide (22 mg, 25%) was obtained by reacting 5-(2-chloromethyl-6,7-dimethoxy-benzofuran-4-ylmethyl)-pyrimidine-2,4-diamine (190 mg, 0.494 mmol) with zinc chloride (67 mg, 0.494 mmol) and the salt of 5-fluoro-1H-indole-2-carboxylic acid dimethylamide obtained by reacting a 3M-solution of ethyl magnesium bromide in diethyl ether (0.98 mL, 2.96 mmol), and 5-fluoro-1H-indole-2-carboxylic acid dimethylamide (613 mg, 2.96 mmol).

MS ESI M/Z:: 519.3 [M+H]+; Structure confirmed by 1H NMR 400 MHz in DMSO-d6.

EXAMPLE 19

3-[4-(2,4-Diamino-pyrimidin-5-ylmethyl)-6,7-dimethoxy-benzofuran-2-ylmethyl]-1H-indole-2-carboxylic acid N,N'-dimethyl-hydrazide (13 mg, 6%) was obtained by reacting 5-(2-chloromethyl-6,7-dimethoxy-benzofuran-4-ylmethyl)-pyrimidine-2,4-diamine (160 mg, 0.416 mmol) with zinc chloride (57 mg, 0.416 mmol) and the salt of 1H-indole-2-carboxylic acid N,N'-dimethyl-hydrazide obtained by reacting a 3M-solution of ethyl magnesium bromide in diethyl ether (0.83 mL, 2.49 mmol), and 1H-indole-2-carboxylic acid N,N'-dimethyl-hydrazide (507 mg, 2.49 mmol).

MS ESI m/z: 516.2 [M+H]+.

EXAMPLE 20

5-Chloro-3-[4-(2,4-diamino-pyrimidin-5-ylmethyl)-6,7-dimethoxy-benzofuran-2-ylmethyl]-1H-indole-2-carboxylic acid methoxy-methyl-amide (8 mg, 2.5%) was obtained by reacting 5-(2-chloromethyl-6,7-dimethoxy-benzofuran-4-ylmethyl)-pyrimidine-2,4-diamine (216 mg, 0.560 mmol) with zinc chloride (76 mg, 0.560 mmol) and a the salt of 5-chloro-1H-indole-2-carboxylic acid methoxy-methyl-amide obtained by reacting a 3M-solution of ethyl magnesium bromide in diethyl ether (1.08 mL, 3.24 mmol), and 5-chloro-1H-indole-2-carboxylic acid methoxy-methyl-amide (771 mg, 3.24 mmol).

MS ESI m/z: 552.1 [M+H]+.

EXAMPLE 21

See Scheme 3

To a solution of [4-(2,4-Diamino-pyrimidin-5-ylmethyl)-6,7-dimethoxy-benzofuran-2-yl]-methanol (1 eq, 2.74 g, 8.3 mmol) in chloroform, Manganese oxide (10 eq, 7.22 g, 83 mmol) was added at room temperature under Argon. The reaction mixture was heated at 45° C. After completion of the reaction, the hot mixture is filtered and the manganese oxide residue is washed with hot acetonitrile. The filtrate is evaporated to give 4-(2,4-diamino-pyrimidin-5-ylmethyl)-6,7-dimethoxy-benzofuran-2-carbaldehyde as a yellow solid (1.63 g, 60%). To a suspension of 4-(2,4-diamino-pyrimidin-5-ylmethyl)-6,7-dimethoxy-benzofuran-2-carbaldehyde (1 eq, 190 mg, 0.58 mmol) and 5-fluoro-1H-indole-2-carboxylic acid methoxy-methyl-amide (2 eq, 886 mg, 1.74 mmol) in Acetic acid (C=0.20 M), a 30% solution of HBr in acetic acid (10 eq, 1.2 mL) was added slowly at 5° C. under Argon. The purple mixture was stirred 20 minutes under Argon until completion. The resulting mixture was poured onto ice water, basified to pH 8 by adding a solution saturated of NaHCO3. After centrifugation of the resulting suspension was filtered and the resulting precipitate was lyophilized overnight. The residue was then digested in methanol to precipitate the amide in excess. After filtration, the filtrate was evaporated to give the compound of formula XII. This compound was used for the next step without further purification.

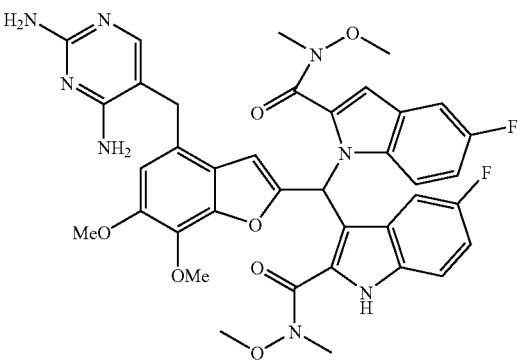

XII

To a solution of the dimere adduct XII (1 eq) in trifluoroacetic acid, boron trifluoride-ethyletherate (3 eq) and triethylsilane (3 eq) were added at 0° C. under Argon. The reaction mixture was then heated at 30° C. until completion. The resulting mixture was poured onto ice, potassium carbonate was added until pH 8. Sodium acetate was added to saturate the medium and the product was extracted with acetonitrile. The organic layer was evaporated and the residue lyophilized overnight. The precipitate obtained was digested in methanol and the resulting filtrate was evaporated. 3-[4-(2,4-Diamino-pyrimidin-5-ylmethyl)-6,7-dimethoxy-benzofuran-2-ylmethyl]-5-fluoro-1H-indole-2-carboxylic acid methoxy-methyl-amide (8.6 mg, 2.7% over the two steps) was obtained after purification by FC, gradient from CH2Cl2 to CH2Cl2/methanol (93/7).

MS ESI m/z: 535.5 [M+H]+

General Procedure E: Measurement of Antimicrobial Activity

Antimicrobial susceptibility testing was performed in accordance with the National Committee for Clinical Laboratory Standards (NCCLS) procedure [M7-A5, 2001]. M7-A5 (2001): Methods for Dilution Antimicrobial Susceptibility Tests for Bacteria That Grow Aerobically; Approved Standard—Fifth Edition American National Standard. The minimal inhibition concentration (MIC) of the compounds regarding resistant strains is in the range of 0.25-2.0 μg/mL depending on the strain used.

General Procedure F: Purified Enzymes and DHFR Enzyme Assay:

Bacterial and human dihydrofolate reductases were purified, shown to be functional and used in DHFR assays as described by Baccanari & Joyner (Baccanari, D. P. and Joyner, S. S. 1981. Dihdrofolate reductase hysteresis and its effect on inhibitor binding analyses. Biochem. 20, 1710-1716)

The IC50 of the compounds regarding DHFR mutants is in the range of 0.5-8.0 μM.

The invention claimed is:

1. A compound of formula I

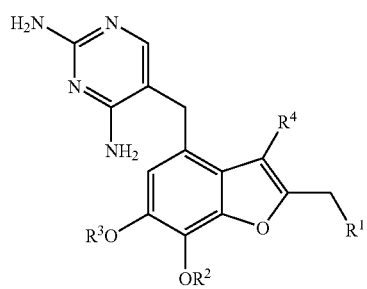

Formula I wherein
$R^1$ represents the groups

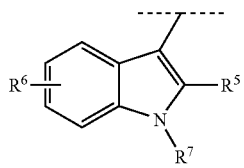

whereby in these groups $R^5$ is hydrogen, lower alkyl with 1 to 4 carbon atoms, or the group

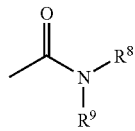

wherein
$R^8$ represents lower alkyloxy, lower alkylamino, or lower alkyl with 1 to 4 carbon atoms;
$R^9$ represents lower alkyl with 1 to 4 carbon atoms;
$R^8$ and $R^9$ together form a 5- or 6-membered heterocyclic ring containing one to two hetero atoms which can be the same or different and are oxygen or nitrogen;
$R^6$ represents hydrogen, halogen, nitro, or lower alkyloxy;
$R^7$ represents hydrogen;
$R^2$ and $R^3$ independently represent hydrogen, lower alkyl with 1 to 3 carbon atoms, or together a lower alkylene group with 1 to 3 carbon atoms bridging the oxygen atoms and forming a five, six or seven membered ring;
$R^4$ represents hydrogen;
or a pharmaceutically acceptable salt thereof.

2. A compound of formula I'

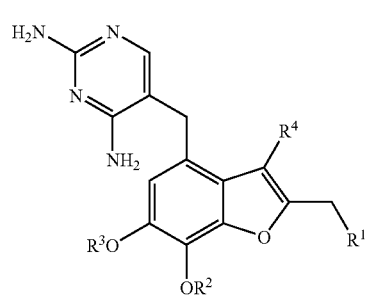

Formula I' wherein
$R^1$ represents the groups

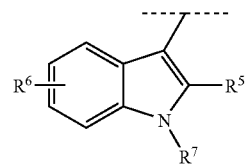

whereby in these groups $R^5$ is hydrogen, lower alkyl with 1 to 4 carbon atoms, or the group

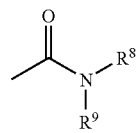

wherein
$R^8$ represents lower alkyloxy, or lower alkyl with 1 to 4 carbon atoms;
$R^9$ represents, lower alkyl with 1 to 4 carbon atoms;
$R^8$ and $R^9$ together form a 5- or 6-membered heterocyclic ring containing one to two hetero atoms which can be the same or different and are oxygen or nitrogen;
$R^6$ represents hydrogen, halogen, nitro, or lower alkyloxy;
$R^7$ represents hydrogen;
$R^2$ and $R^3$ independently represent hydrogen, lower alkyl with 1 to 3 carbon atoms, or together a lower alkylene group with 1 to 3 carbon atoms bridging the oxygen atoms and forming a five, six or seven membered ring;
$R^4$ represents hydrogen;
or a pharmaceutically acceptable salt thereof.

3. A compound of formula II

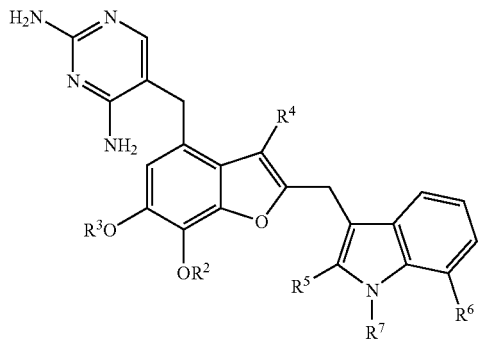

Formula II wherein
$R^2$ and $R^3$ represent methyl;
$R^4$ represents hydrogen;
$R^5$ is hydrogen, lower alkyl with 1 to 4 carbon atoms, or the group

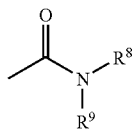

wherein
$R^8$ represents lower alkyloxy, lower alkylamino, or lower alkyl with 1 to 4 carbon atoms;
$R^9$ represents lower alkyl with 1 to 4 carbon atoms;
$R^8$ and $R^9$ together form a 5- or 6-membered heterocylic ring containing one to two hetero atoms which can be the same or different and are oxygen or nitrogen;
$R^6$ represents hydrogen, halogen, nitro, or lower alkyloxy;
$R^7$ represents hydrogen;
or a pharmaceutically acceptable salt thereof.

4. A compound of formula III

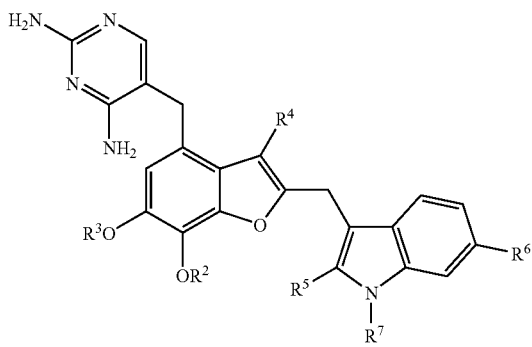

Formula III wherein
$R^2$ and $R^3$ represent methyl;
$R^4$ represents hydrogen;
$R^5$ is hydrogen, lower alkyl with 1 to 4 carbon atoms, or the group

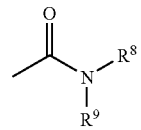

wherein
$R^8$ represents lower alkyloxy, lower alkylamino, or lower alkyl with 1 to 4 carbon atoms;
$R^9$ represents lower alkyl with 1 to 4 carbon atoms;
$R^8$ and $R^9$ together form a 5- or 6-membered heterocylic ring containing one to two hetero atoms which can be the same or different and are oxygen or nitrogen;
$R^6$ represents hydrogen, halogen, nitro, or lower alkyloxy;
$R^7$ represents hydrogen;
or a pharmaceutically acceptable salt thereof.

5. A compound of formula IV

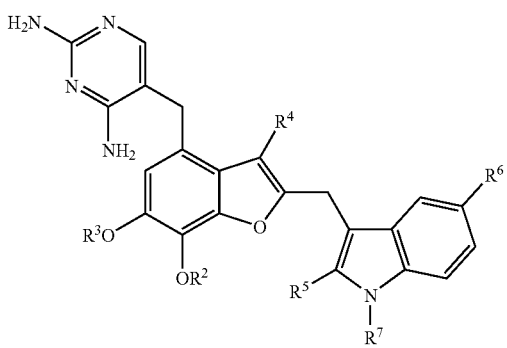

Formula IV wherein
$R^2$ and $R^3$ represent methyl;
$R^4$ represents hydrogen;
$R^5$ is hydrogen, lower alkyl with 1 to 4 carbon atoms, or the group

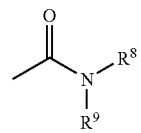

wherein
$R^8$ represents lower alkyloxy, lower alkylamino, or lower alkyl with 1 to 4 carbon atoms;
$R^9$ represents lower alkyl with 1 to 4 carbon atoms;
$R^8$ and $R^9$ together form a 5- or 6-membered heterocylic ring containing one to two hetero atoms which can be the same or different and are oxygen or nitrogen;
$R^6$ represents hydrogen, halogen, nitro, or lower alkyloxy;
$R^7$ represents hydrogen;
or a pharmaceutically acceptable salt thereof.

6. The compound of claim 1 selected from the group consisting of:
- 5-[6,7-Dimethoxy-2-(7-methoxy-1H-indol-3-ylmethyl)-benzofuran-4-ylmethyl]-pyrimidine-2,4-diamine;
- 5-[6,7-Dimethoxy-2-(5-methoxy-1H-indol-3-ylmethyl)-benzofuran-4-ylmethyl]-pyrimidine-2,4-diamine;
- 5-[2-(1H-Indol-3-ylmethyl)-6,7-dimethoxy-benzofuran-4-ylmethyl]-pyrimidine-2,4-diamine;
- 5-[6,7-Dimethoxy-2-(2-methyl-1H-indol-3-ylmethyl)-benzofuran-4-ylmethyl]-pyrimidine-2,4-diamine;
- 5-[2-(6-Fluoro-1H-indol-3-ylmethyl)-6,7-dimethoxy-benzofuran-4-ylmethyl]-pyrimidine-2,4-diamine;
- {3-[4-(2,4-Diamino-pyrimidin-5-ylmethyl)-6,7-dimethoxy-benzofuran-2-ylmethyl]-1H-indol-2-yl}-morpholin-4-yl-methanone;
- 3-[4-(2,4-Diamino-pyrimidin-5-ylmethyl)-6,7-dimethoxy-benzofuran-2-ylmethyl]-1H-indole-2-carboxylic acid dimethylamide;
- 5-[6,7-Dimethoxy-2-(5-nitro-1H-indol-3-ylmethyl)-benzofuran-4-ylmethyl]-pyrimidine-2,4-diamine;
- {3-[4-(2,4-Diamino-pyrimidin-5-ylmethyl)-6,7-dimethoxy-benzofuran-2-ylmethyl]-1H-indol-2-yl}-pyrrolidin-1-yl-methanone;
- 3-[4-(2,4-Diamino-pyrimidin-5-ylmethyl)-6,7-dimethoxy-benzofuran-2-ylmethyl]-5-methoxy-1H-indole-2-carboxylic acid dimethylamide;
- 3-[4-(2,4-Diamino-pyrimidin-5-ylmethyl)-6,7-dimethoxy-benzofuran-2-ylmethyl]-1H-indole-2-carboxylic acid methoxy-methyl-amide;
- 5-Chloro-3-[4-(2,4-diamino-pyrimidin-5-ylmethyl)-6,7-dimethoxy-benzofuran-2-ylmethyl]-1H-indole-2-carboxylic acid dimethylamide;
- 3-[4-(2,4-Diamino-pyrimidin-5-ylmethyl)-6,7-dimethoxy-benzofuran-2-ylmethyl]-5-fluoro-1H-indole-2-carboxylic acid dimethylamide;
- 5-Chloro-3-[4-(2,4-diamino-pyrimidin-5-ylmethyl)-6,7-dimethoxy-benzofuran-2-ylmethyl]-1H-indole-2-carboxylic acid methoxy-methyl-amide;
- 3-[4-(2,4-Diamino-pyrimidin-5-ylmethyl)-6,7-dimethoxy-benzofuran-2-ylmethyl]-1H-indole-2-carboxylic acid N,N'-dimethyl-hydrazide;
- 3-[4-(2,4-Diamino-pyrimidin-5-ylmethyl)-6,7-dimethoxy-benzofuran-2-ylmethyl]-5-fluoro-1H-indole-2-carboxylic acid methoxy-methyl-amide;

or a pharmaceutically acceptable salt thereof.

7. An intermediate compound of formula XI and XII

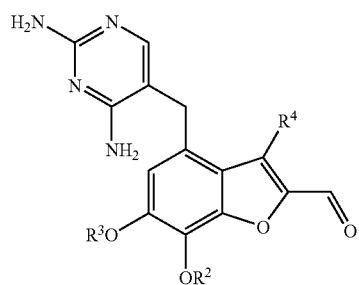

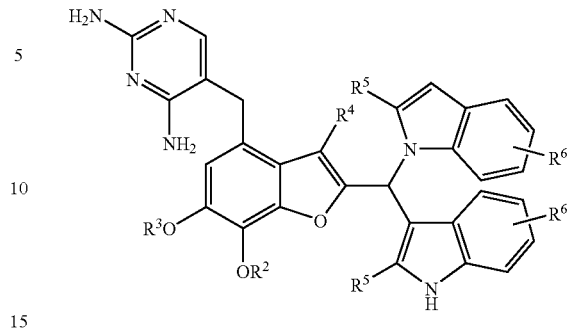

wherein
$R^2$ and $R^3$ independently represent hydrogen, lower alkyl with 1 to 3 carbon atoms, or together a lower alkylene group with 1 to 3 carbon atoms bridging the oxygen atoms and forming a five, six or seven membered ring;
$R^4$ represents hydrogen;
$R^5$ is hydrogen, lower alkyl with 1 to 4 carbon atoms, or the group

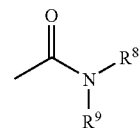

wherein
$R^8$ represents lower alkyloxy, lower alkylamino, or lower alkyl with 1 to 4 carbon atoms;
$R^9$ represents lower alkyl with 1 to 4 carbon atoms;
$R^8$ and $R^9$ together form a 5- or 6-membered heterocyclic ring containing one to two hetero atoms which can be the same or different and are oxygen or nitrogen;
$R^6$ represents hydrogen, halogen, nitro, or lower alkyloxy.

8. A pharmaceutical composition comprising one or more compounds of claim 1 and a pharmaceutically acceptable inert carrier material.

9. A process for the manufacture of a pharmaceutical composition containing one or more compounds as claimed in claim 1 as active ingredients, which process comprises mixing one or more active ingredients with a pharmaceutically acceptable inert carrier material and/or an adjuvant.

10. A process for the manufacture of a pharmaceutical composition comprising one or more compounds as claimed in claim 6 as active ingredients, which process comprises mixing one or more active ingredients with a pharmaceutically acceptable inert carrier material and/or an adjuvant.

11. A pharmaceutical composition comprising one or more compounds of claim 6 and a pharmaceutically acceptable inert carrier material.

12. A method for treating an infection caused by a bacterium that can be inhibited through inhibition of its dihydrofolate reductdase enzyme by administering to a subject in need thereof an effective amount of the compound of claim 1.

13. The method of claim 12, wherein the bacterium is a Gram positive pathogen or a Gram negative pathogen.

14. A method for treating an infection caused by a bacterium that can be inhibited through inhibition of its dihydrofolate reductdase enzyme by administering to a subject in need thereof an effective amount of the compound of claim 6.

15. The method of claim 14, wherein the bacterium is a Gram positive pathogen or a Gram negative pathogen.

* * * * *